United States Patent [19]

Simoncsits et al.

[11] Patent Number: 5,183,748

[45] Date of Patent: Feb. 2, 1993

[54] PROCESS FOR THE PREPARATION OF OLIGO- AND POLYDEOXYRIBONUCLEOTIDES

[76] Inventors: András Simoncsits; Miklós Kálmán; Csaba Kari; Imre Cserpán, all of Szeged, Hungary

[73] Assignee: Vepex Contractor LTD., Budapest; MTA Szegedi Biologiai Kozpontja, Odesszai, both of Hungary

[21] Appl. No.: 800,669

[22] Filed: Nov. 22, 1985

[30] Foreign Application Priority Data

Nov. 23, 1984 [HU] Hungary .............................. 4356/84

[51] Int. Cl.⁵ ...................... C12P 19/34; C12N 15/00; C07H 15/12
[52] U.S. Cl. .................... 455/91; 435/172.3; 435/320.1; 536/24.2
[58] Field of Search ...................... 435/91, 172.3, 320, 435/320.1; 536/27

[56] References Cited

U.S. PATENT DOCUMENTS 4,666,839  5/1987  Souza .................................. 435/91

OTHER PUBLICATIONS

Messing et al. 1981. Nucl. Acids Res. 9(2): 309-321.
Messing et al. 1982. Crene 19:269-276.
Rossi et al. 1982. J. Biol. Chem. 257(16):9226-9229.

Primary Examiner—Elizabeth C. Weimar
Assistant Examiner—David T. Fox
Attorney, Agent, or Firm—Keil & Weinkauf

[57] ABSTRACT

The invention relates to a process for the preparation of oligo- and polydeoxyribonucleotides by synthesizing the complementary strand of a single-stranded DNA piece enzymatically, in the presence of deoxyribonucleoside 5'-triphosphates in a cloning vector.

10 Claims, 15 Drawing Sheets where dNTP is an equimolar mixture of all four deoxyribonucleoside 5' triphosphates where dNTP is an equimolar mixture of all four deoxyribonucleoside 5' triphosphates where: N is any of the four deoxyribonucleotides, and n ≥ 1 is the number of N residues

Figure 6 pTTTACCAGCTTGAGAACTACTGTAACTAGCCTGCA

+ pGCGGGGGCA
GACGTCGCCCCCGTTCGAp

→ T4 DNA ligase
Hind III pTTTACCAGCTTGAGAACTACTGTAACTAGCCTGCAGCGGGGGCA
GACGTCGCCCCCGTTCGAp

Figure 8

Sequence of M13 mp W324 betwen BamHI and Pst I sites:

```
-GGATCCGTCGACCTGCAG-
-CCTAGGCAGCTGGACGTC-
  ‾‾‾‾                ‾‾‾‾‾
  BamHI               Pst I
```

Sequence of M13 mp 8 betwen BamHI and Pst I sites:

```
-GGATCCCTGACCTCCTGCAG-
-CCTAGGGACTGGAGGACGTC-
  ‾‾‾‾‾                ‾‾‾‾‾
  BamHI                Pst I
```

PROCESS FOR THE PREPARATION OF OLIGO- AND POLYDEOXYRIBONUCLEOTIDES

The invention relates to a process for the preparation of oligo- and polydeoxyribonucleotides by synthesizing the complementary strand of a single-stranded DNA piece enzymatically, in the presence of deoxyribonucleoside 5'-triphosphates in a cloning vector.

The vectors and adapters used in the synthesis in accordance with the invention also fall within the scope of the invention.

As concerns the basic research in organic chemistry during the past 20 years, an outstanding role has been played by the chemical synthesis of oligodeoxyribonucleotides containing a specific nucleotide sequence (Khorana HG 1979 Science 203, 614; Itakura K and Riggs AD 1980 Science 209, 1401).

Besides their importance in basic research, these compounds have recently become indispensable in the biotechnological applications of the rapidly developing field of genetic engineering. The multiple application of synthetic DNA pieces has opened up new prospects for in vitro DNA recombination. Application possibilities include, for example, the use of various linking regions, such as restriction linkers and adapters, hybridization probes for the identification or isolation of certain genes, and oligodeoxyribonucleotides suitable for the site-specific in vitro mutagenesis of cloned genes, etc. The synthesis of DNA regions playing an important role in the regulation of transcription and translation is of high importance with respect to the gene expression. One of the most demanding applications of DNA synthesis is the total chemical synthesis of certain genes (which may be either natural genes or artificial genes specifically designed for the optimal production of certain proteins in a given microorganism). This application is of particular importance if the given gene is difficult to isolate from a natural source, or if the information coded by it results in a different product from the desired one in the organism chosen for gene expression.

It is not surprising, therefore, that in the past few years many attempts have been made to speed up and simplify the techniques of chemical DNA synthesis. The primary aims of these attempts were the selection of optimal protecting groups, the increase of the rates and yields of coupling reactions, the utilization of synthetic intermediates without further purification and effective techniques for purification of the end-product. The application of optimal protecting groups and the performance of the coupling reactions on appropriately selected solid supports have opened up the possibility of the manufacture of semi-automatic and automatic DNA synthesizers.

However quick and efficient the above methods may be, they are generally suitable only for the preparation of single-stranded DNA fragments containing up to at most about 100 nucleotides depending on the apparatus employed. Further, the physico-chemical separation and purification techniques (e.g. gel electrophoresis and chromatography, including HPLC) developed for the processing of the oligomers obtained in this way do not necessarily result in a biochemically uniform, homogeneous end-product.

To overcome the above-mentioned limits and disadvantages of the chemical processes, the combined use of chemical and enzymatic methods and combination of these with cloning techniques have been suggested. The synthesis is simplified substantially if only one strand of the DNA fragment to be synthesized is prepared chemically, while the complementary strand is built up partially or entirely by enzymatic methods. This procedure not only shortens the time required for the synthesis of the desired DNA fragment, but also renders the process considerably more economic, since the precursors of enzymatic synthesis, deoxyribonucleoside 5'-triphosphates, are required in an amount lower by orders 4-5 of magnitude than the starting materials of chemical synthesis.

One of the combined chemical-enzymatic solutions is based on the discovery that the large fragment of E.coli DNA polymerase I (Klenow polymerase) is capable of converting a partially double-stranded DNA region into a fully double-stranded one in the presence of all four deoxyribonucleoside 5'-triphosphates, so that the longer DNA strand serves as a template while the shorter DNA strand serves as a primer, and the process is performed in the 5'→3' direction, up to the length of the template (Maniatis T, Fritsch EF and Sambrook J 1982 Molecular Cloning, Cold Spring Harbor Laboratory, N.Y. pp. 113-116). Utilizing this finding, Itakura et al. (Rossi JJ, Kierzek R, Huang T, Walker PA and Itakura K 1982 J. Biol. Chem. 257, 9226) prepared two relatively long (39-43-mer) oligonucleotides chemically, which at their 3'-ends contained complementary regions 9-10 base pairs long. A double-stranded fragment containing 72 base pairs was prepared by annealing the two single-stranded oligonucleotides and performing the filling-in reaction with Klenow polymerase in the presence of all four deoxyribonucleoside 5'-triphosphates.

A similar procedure was applied in Narang's laboratory (Scarpulla RS, Narang SA and Wu R 1982. Anal. Biochemistry 121, 356) during the synthesis of the artificial gene coding for chain A of human insulin, with the major difference that reverse transcriptase was used to fill in the double strand.

The double-stranded DNA fragments obtained by any of the above methods are then cloned in a vector. Since it is advisable to cleave the cloning vector with two restriction endonucleases which have different specificities and which each cleave the given vector only once, the DNA region to be cloned should be supplied with the appropriate terminal sections. This may be accomplished by the addition of two different restriction linkers to the two ends of the double-stranded DNA and by subsequent digestion with the two corresponding restriction enzymes to obtain the two sticky ends suitable for cloning (Scarpulla RS, Narang SA and Wu R 1982 Anal. Biochemistry 121, 356). Scarpulla et al. obtained a 75 base pair DNA fragment suitable for oriented insertion. If a longer DNA fragment is to be prepared and cloned, it is simpler and more economic to prepare two double-stranded DNA pieces, one of which contains the cleavage site corresponding to one of the restriction enzymes at its 5'-end, while the other contains the cleavage site corresponding to the other restriction enzyme at its 3'-end (Rossi JJ, Kierzek R, Huang T, Walker PA and Itakura K 1982 J. Biol. Chem. 257, 9226). The two DNA pieces are then cleaved separately with the corresponding restriction enzymes. Through combination of these with the appropriately cleaved cloning vector, performance of a triple ligation and transformation into a suitable E.coli strain, a recombinant is obtained in which the cloning vector contains the two DNA pieces linked to each other as desired.

The disadvantages of the hitherto-known processes outlined above are as follows: 1. The chemically synthesized DNA pieces each have to contain the overlapping regions required for annealing (9-10 nucleotides) at their 3'-end, and the restriction sites and a further 2-4 nucleotide section necessary for effective cleavage at the restriction sites (altogether further 8-10 nucleotides for each synthetic DNA piece). With respect to the end-product the synthesis of these sections may be considered superfluous. 2. Both the single-stranded oligonucleotides and the filled-in double-stranded DNA fragment should be purified before cloning.

The invention relates to a new process in which the complementary strand of the chemically synthesized single-stranded DNA piece is prepared entirely enzymatically, but the above disadvantages are being eliminated.

In the process described in the invention, a chemically synthesised single-stranded oligodeoxyribonucleotide is ligated to a suitably cut cloning vector either directly or by means of an appropriate adapter. The vector modified in this way functions as a primer-template system in the filling-in reaction catalysed by the polymerase, so that the single-stranded region ligated to the vector serves as a template, while the vector strand that is non-ligated or ligated only to the adapter serves as a primer. Accordingly, the complementary strand is synthesized entirely enzymatically, and, since the whole process is linked to a vector, direct cloning of the double-stranded region obtained becomes possible. The invention therefore relates to a process for the preparation of oligo- and polydeoxyribonucleotides through the enzymatic synthesis of the complementary strand of a single-stranded DNA piece in the presence of deoxyribonucleoside 5'-triphosphates, this enzymatic process being carried out in a cloning vector.

BRIEF DESCRIPTION OF THE DRAWINGS

FIG. 6 shows ligation of the 35-mer compound to the PstI/Hind III adapter.

FIG. 8 shows sequences between BamHi and Pst8 sites in M13 mp W324 and M13 mp8.

Figure 1:
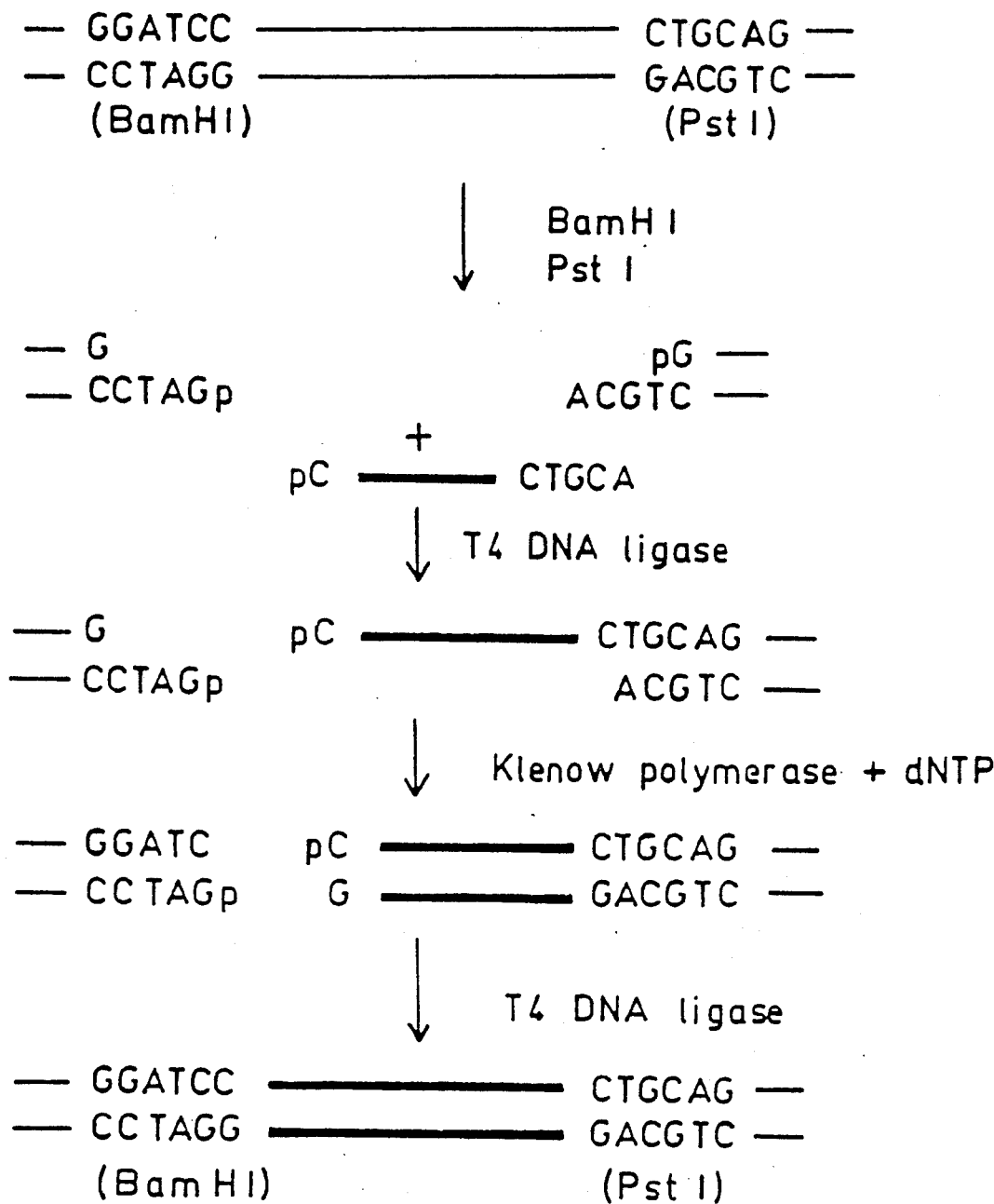
FIG. 1 shows a process wherein the chemically synthesized single-stranded DNA fragment having a 5'-phosphate group and a 3'-terminal sequence complementary to a 3'-protruding end of a cleaved vector is ligated directly to the vector by means of T4 DNA ligase.

In one of the preferred variants of the process, the vector having two unique restriction sites is cleaved with the two corresponding restriction enzymes to obtain a 5'-protruding end and a 3'-protruding end, respectively. The chemically synthesized single-stranded DNA fragment having a 5'-phosphate group and a 3'-terminal sequence complementary to the 3'-protruding end of the cleaved vector is ligated directly to the vector by means of T4 DNA ligase (FIG. 1). (The 5'-terminal sequence of the synthetic single-stranded DNA fragment is not complementary to the 5'-protruding end of the cleaved vector.) After ligation, the linear vector contains 5'-protruding regions at both ends, one of these originating from the cleavage, and the other from the linking of the 3'-protruding end with the synthetic single-stranded DNA fragment. The 5'-protruding ends are then filled in with the large fragment of E.coli DNA polymerase I (Klenow polymerase) in the presence of all four 5'-triphosphates. It can be seen that the complementary strand of the synthetic single-stranded DNA fragment is synthesized enzymatically, in a cloning vector, so that the non-ligated strand of the vector serves as a primer.

The linear, modified vector, which is filled in at both ends (blunt ends), is circularized with T4 DNA ligase.

Thereafter, appropriately treated bacterium cells (E.coli) are transformed with the ligation mixture obtained by the above steps.

The desired recombinants are next selected by double selection. One of the selection markers is a property based on the presence of a cloning vector (e.g. plaque formation in the case of a phage vector, or the formation of antibiotic-resistant colonies in the case of a plasmid vector), while the other selection marker is a phenotype property caused in the obtained recombinant by the incorporation of the DNA sequence to be cloned (e.g. modification of plaque formation, loss of antibiotic resistance). A further selection possibility is the colony or plaque hybridization method, when the radioactively labeled, single-stranded DNA fragment to be cloned serves as a hybridization probe.

The selected clones, containing in high probability both the synthetic DNA fragment and its complementary strand, are identified by means of a partial or total DNA sequencing. For the simultaneous screening of a large number of recombinants, the dideoxy chain-termination process can be employed advantageously (Sanger F, Nicklen S and Coulson AR 1977 PNAS USA 74, 5463).

Figure 2:
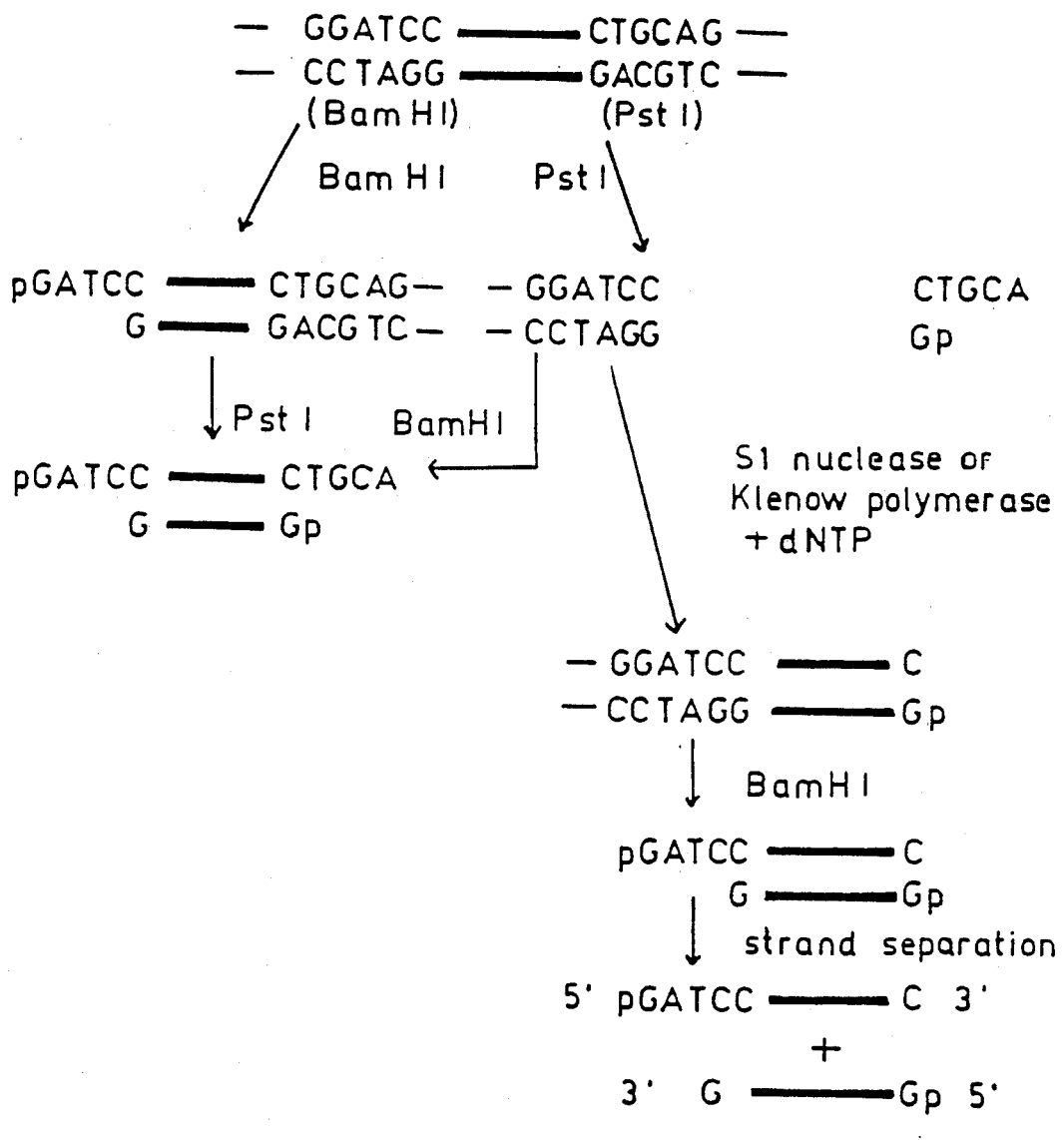
FIG. 2 shows the use of enzymes to cleave the cloned double-stranded DNA regions from the vector and separating the DNA double strands to prepare single-stranded DNA pieces in which the ends correspond to the enzymes used.

The recombinant vector is isolated from the selected clones in a known manner (see e.g. Birnboim HC and Doly J 1979 Nucleic Acids Res. 7, 1513; Messing J, Crea R and Seeburg PH 1981 Nucleic Acids Res. 9, 309). The cloned double-stranded DNA region can be cleaved off the vector obtained by means of the starting enzymes, provided that the sequence of the DNA region is such that its insertion restores the bordering restriction sites (a given nucleotide at the 5'-end and a sequence of five nucleotides at the 3'-end). Depending on the subsequent use, these enzymes may be employed simultaneously or consecutively in a suitable order, or they may be combined with other enzymatic steps (e.g. S1 nuclease or Klenow polymerase and deoxynucleoside 5'-triphosphates), to yield partially double-stranded, totally double-stranded or (after strand separation) single-stranded DNA pieces, with ends corresponding to the enzymes employed (FIG. 2).

In one of the preferred variants of the invention, the above cloning process is repeated in a cyclic manner with a number of oligodeoxyribonucleotides, during which the individual oligodeoxyribonucleotides are joined to one another inside the cloning vector. This particular variant of the invention can be carried out in two alternative ways:

The first cloned oligodeoxyribonucleotide may be isolated in a partially double-stranded form, combined with the second, single-stranded oligodeoxyribonucleotide and cloned again, either in the original cloning vector or in another vector selected to be advantageous for the second cloning (route A).

Alternatively, the first cloned oligodeoxyribonucleotide may be left in the recombinant vector, which is then cleaved so that the ligation of the second oligodeoxyribonucleotide to the vector, its linking to the first oligodeoxyribonucleotide inside the vector and the cloning of the two linked oligodexyribonucleotides becomes possible (route B).

Route A

Figure 3A:
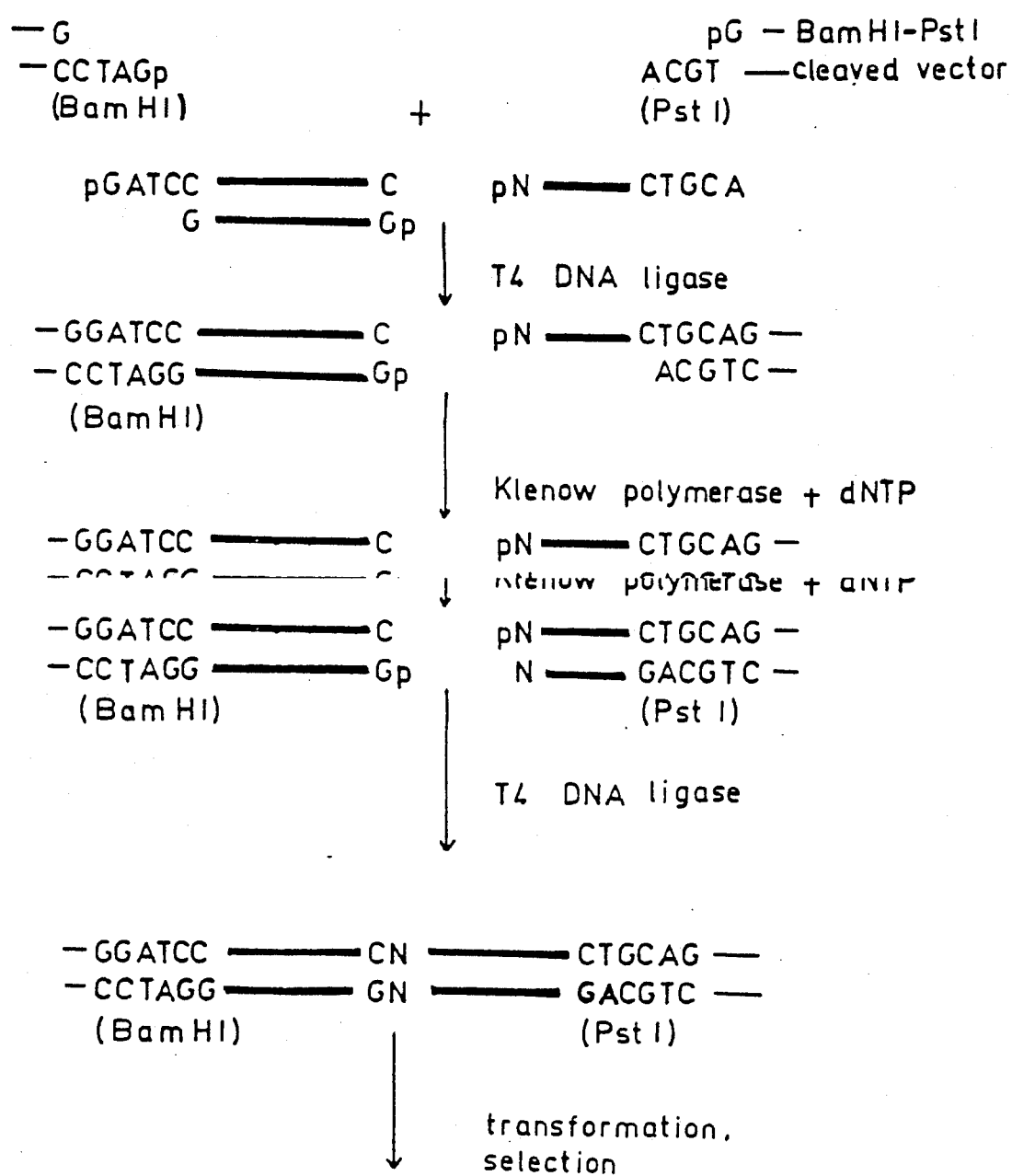
FIGS. 3a and 3b show linking of a first oligodeoxyribonucleotide to a second, single-stranded oligodeoxyribonucleotide and a second cloning which is carried out either in the original cloning vector or in another cloning vector to transform and select the desired recombinants.
Figure 3B:
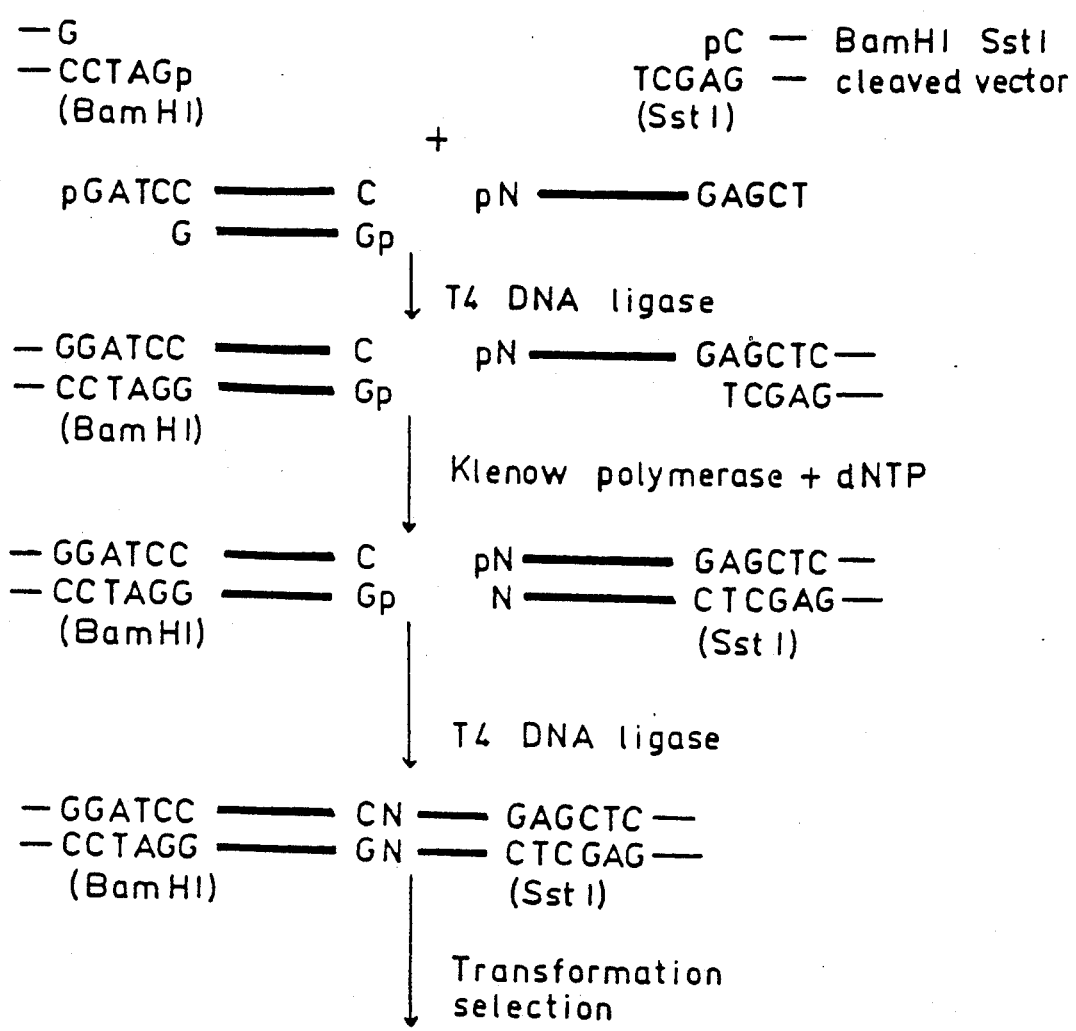

If the first cloned oligodeoxyribonucleotide is isolated by cleavage from the cloning vector (FIG. 2; PstI, S1 nuclease or Klenow polymerase+deoxynucleoside 5'-triphosphates, followed by BamHI steps), its linking to the second, single-stranded oligodeoxyribonucleotide and second cloning can be carried out either in the original cloning vector or in another cloning vector appropriate for the selection of the expected recombinants (FIGS. 3a and 3b). It should be noted that it is not usually necessary to use a vector resulting in a new 3'-protruding end (e.g. SstI in place of PstI in FIG. 3b). This may be required only during the synthesis of a long DNA piece, e.g. an artificial gene if the otherwise flexible use of the genetic code does not allow the presence of a C nucleotide instead of a G nucleotide at the 3'-end of the intermediate DNA fragment obtained after two cycles (see FIGS. 3a and 3b for the second cycle). The isolation of this intermediate according to FIG. 2 would result in a partial duplex with C nucleotide or G nucleotide at the 3'-end, depending on the vector used in the second cycle (the BamHI-PstI vector results in C, while the BamHI-SstI vector results in G at the 3'-end according to FIGS. 3a and 3b, respectively).

The disadvantages of route A are that the first cloned oligodeoxyribonucleotide should be isolated from the recombinant vector (FIG. 2) and it should be joined to the second oligodeoxyribonucleotide by means of the original (FIG. 3a) or a different (FIG. 3b) cloning vector. Such a triple ligation and the following steps may result in recombinants lacking either the first or the second oligodeoxyribonucleotide.

Route B eliminates these disadvantages.

Route B

If the first cloned oligodeoxyribonucleotide remains part of the recombinant vector, the linking of the first cloned oligodeoxyribonucleotide with a second (third, etc.) oligodeoxyribonucleotide and its cloning in the same vector may be performed in two alternative ways.

Route B1

Figure 4:
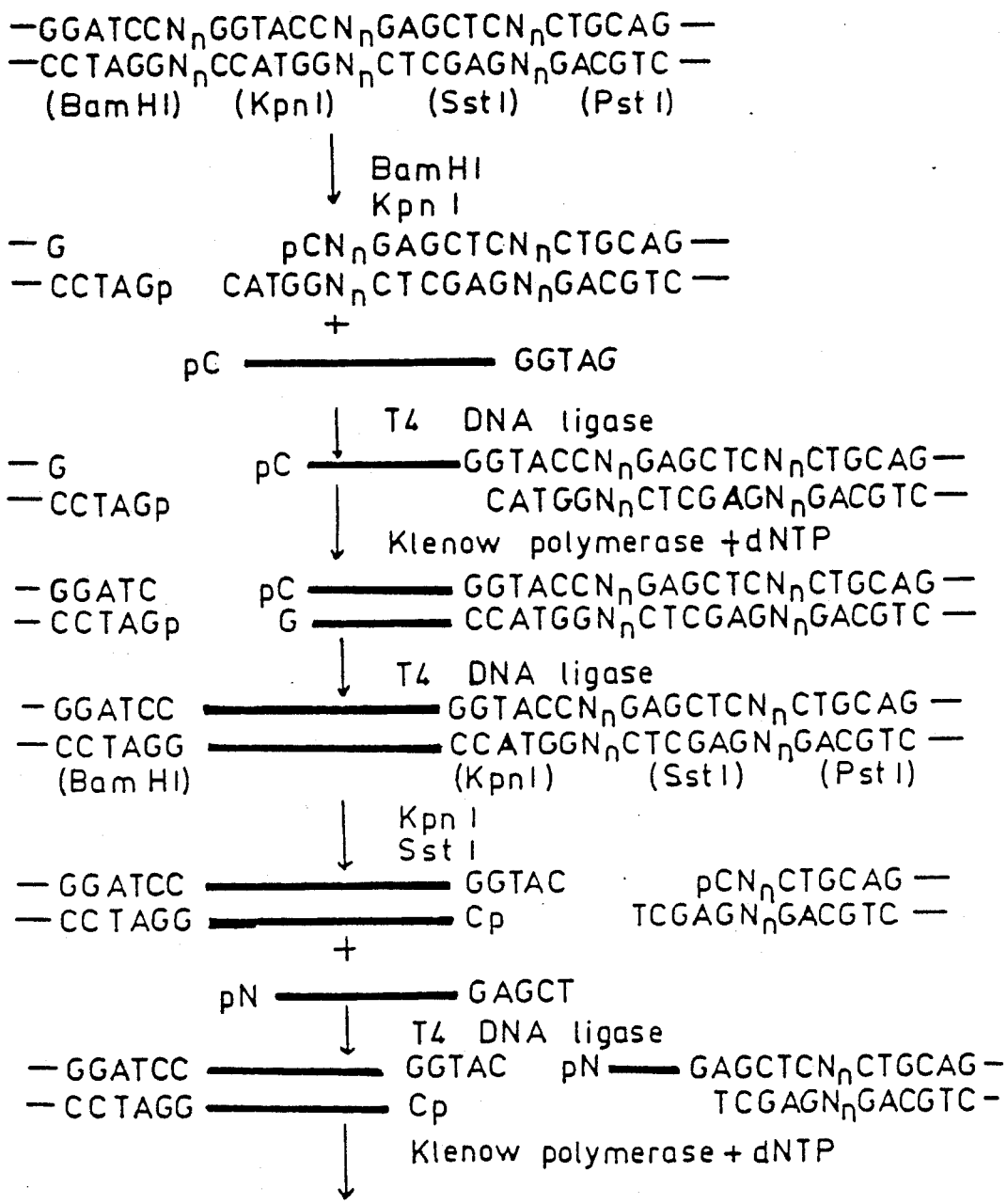
FIG. 4 shows a schematic outline of Route B1.
Figure 4:
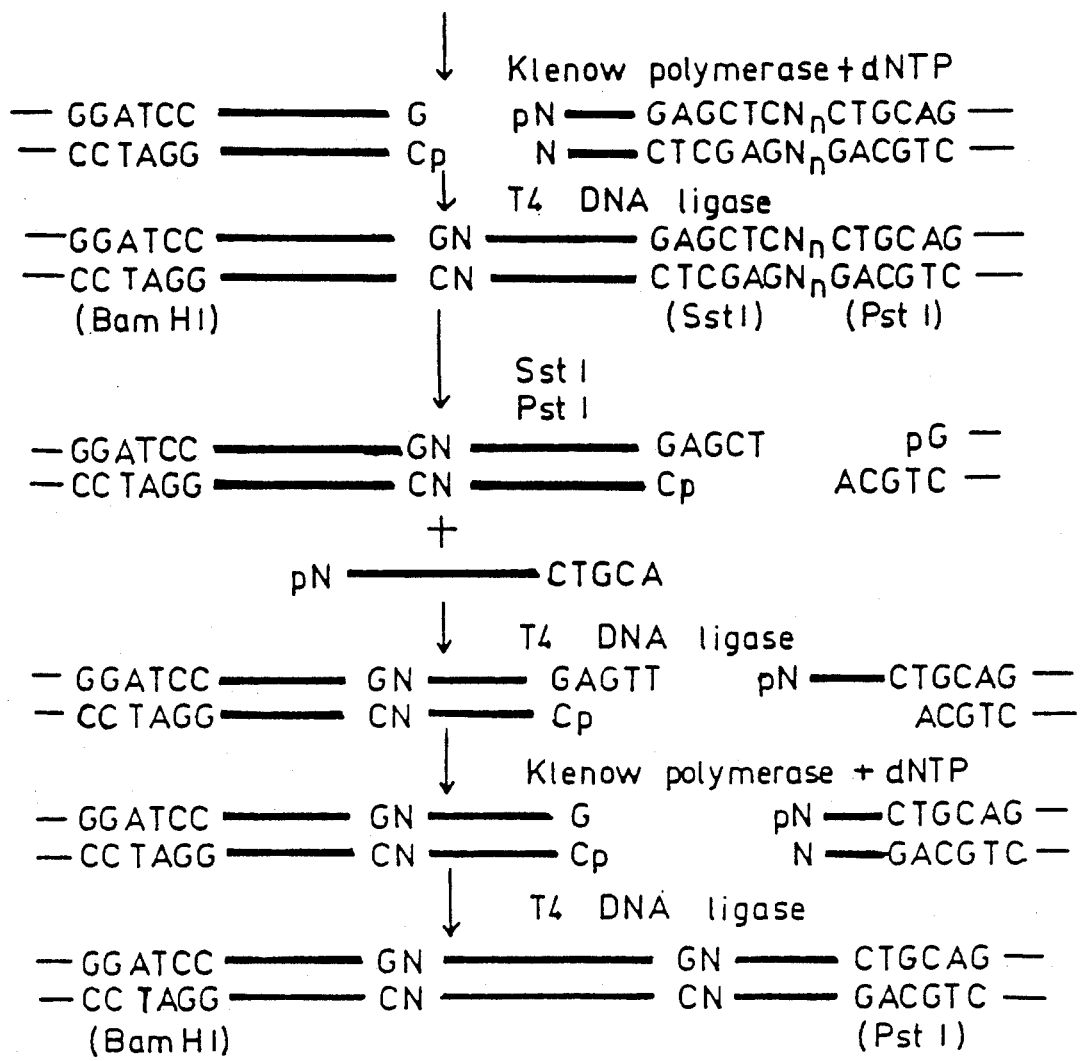

In the first alternative, special vectors are constructed and employed; these contain a number of closely located cleavage sites giving a 3'-protruding end, each being present only once in the vector, preferably in such an arrangement that the enzymatic steps following cloning leave only one or two nucleotides of the restriction sites at the attachment points of the synthetic DNA fragments (FIG. 4). This is not a strong limitation, however, since these nucleotides can be incorporated into the desired DNA through an appropriate choice of the length of the chemically synthesized DNA fragment and by making use of the degeneration of the genetic code.

FIG. 4 illustrates the use of route B1, starting from a vector containing four closely-situated, unique restriction sites. One of the four sites results in a 5'-protruding end (BamHI), and the other three in 3'-protruding ends (KpnI, SstI, PstI). The first step of cyclic application (BamHI, KpnI cleavage, etc.) is performed essentially as illustrated in FIG. 1 and yields a recombinant which contains the first oligodeoxyribonucleotide between the sites BamHI and KpnI. In the second step the recombinant is first cleaved with enzymes KpnI and SstI, and the linear vector obtained is purified. The following oligodeoxyribonucleotide, containing a sequence complementary to the site SstI at its 3'-end, is ligated to the site SstI of the vector. The ligated single-stranded region is then filled in with Klenow polymerase in the presence of all four deoxynucleoside 5'-triphosphates, while the non-ligated 3'-protruding end derived from the KpnI cleavage is eliminated by the 3'→5' exonuclease activity of the Klenow polymerase (Maniatis T, Fritsch EF and Sambrook J 1982 Molecular Cloning, Cold Spring Harbor Laboratory N.Y., pp 113–116). The linear vector obtained is recircularized with T4 DNA ligase (blunt end ligation) to yield a modified vector containing the first oligodeoxyribonucleotide between sites BamHI and KpnI and the second oligodeoxyribonucleotide between sites KpnI and SstI of the original vector so that the two oligodeoxyribonucleotides are linked with each other and only one nucleotide (G) remains from the site KpnI serving for the first ligation. In the third step the vector is first cleaved with SstI and PstI and, after purification, the third single-stranded oligodeoxyribonucleotide, containing a sequence characteristic of PstI cleavage at its 3'-end, is ligated to site PstI. After the enzymatic reactions described in connection with step two, a vector containing all three interlinked oligodeoxyribonucleotides is obtained. In the resulting DNA region there is only one nucleotide (G) from site KpnI and another one (G) from site SstI, and this region is surrounded by the two outside cleavage sites (BamHI, PstI) also present in the original vector. Accordingly, the linked and cloned DNA region can be cut out by these enzymes, and may be treated as illustrated in FIG. 2, for example, depending on the further use intended.

Route B2

If route B1 is followed, the maximum number of cycles is obviously limited by the number of the various specific cleavage sites, and this number must be finite even if the vector is constructed ideally. Accordingly, it is desirable to develop a cloning system which allows an infinite repetition of synthetic cycles.

We have found that this can be achieved by using a synthetic adapter, which is capable of ligation with the synthetic DNA piece to be cloned and of linking the ligate obtained to the cloning vector, and which can always be eliminated completely from the recombinants in the same manner after each cloning step.

The above requirements are met by a partially double-stranded DNA piece containing a 3'-and a 5'-protruding end, respectively, at its two ends. The 5'-protruding end of the adapter is complementary to that of the linearized vector cleaved by an appropriate restriction enzyme, and the 3'-protruding end of the adapter is characteristic of a restriction enzyme the recognition sequence of which is not present in the linearized vector. The length of the double-stranded region of the adapter may be varied within wide limits; it preferably contains between 8 and 10 base pairs. This length results in a satisfactorily stable duplex. Further, when the length of the double-stranded region of the adapter is considered, care must be taken that the selection property connected with the vector employed should remain unchanged. For instance, if the adapter becomes part of a DNA region coding for a fusion protein during the selection step, the enzyme activity taken as the basis of selection must not be influenced (incorporation of the adapter should not cause a shift in the reading frame). At the same time, the adapter must not contain a termination triplet in the reading frame.

The vector to be used in route B2 should contain two unique restriction sites with different specificities. One of these results in a 5'-protruding end, complementary to the 5'-protruding end of the ligate formed from the adapter and the single-stranded oligodeoxyribonucleotide to be cloned. The other restriction site results in a 5'-protruding end, too, which is filled in simultaneously with the filling-in of the single-stranded region to be cloned, as illustrated in FIG. 1.

Figure 5:
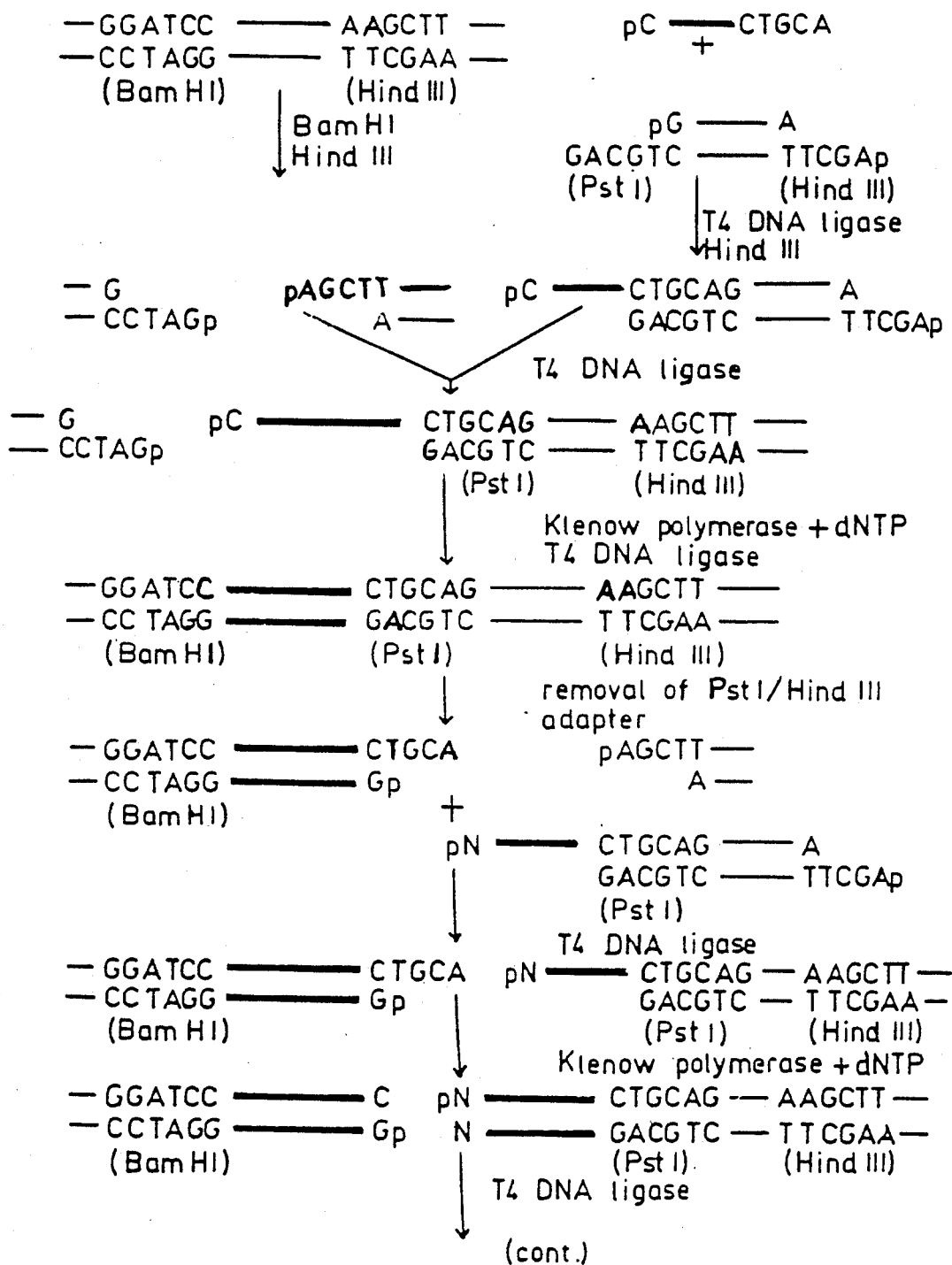
FIG. 5 shows a schematic outline of Route B2.
Figure 5:
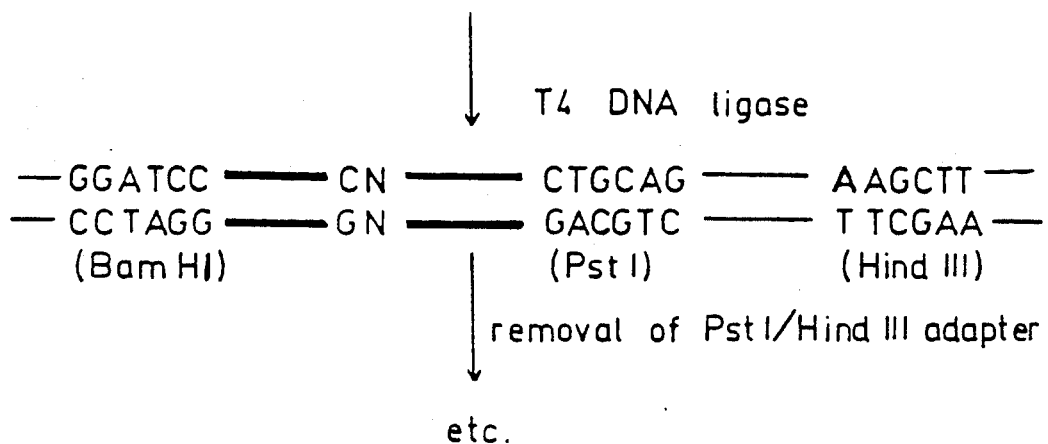

Route B2 is outlined schematically in FIG. 5. The starting vector is cleaved with two restriction enzymes, resulting in 5'-protruding ends with different specificities (BamHI and HindIII). In the meantime, the single-stranded oligodeoxyribonucleotide is ligated to the site PstI of the synthetic adapter having PstI and HindIII ends. Since self-ligation of adapter molecules may also take place during ligation at site HindIII, the reaction mixture is treated with HindIII enzyme, and the single-stranded oligodeoxyribonucleotide-adapter ligate is isolated and then ligated to site HindIII of the BamHI-HindIII cleaved vector. The single-stranded regions of the resulting vector are next filled in and the vector is circularized. After transformation into competent E. coli cells and selection, the recombinant vector is isolated. The vector obtained is cleaved at the sites PstI and HindIII, and the linearized vector is separated from the adapter molecule. In the second cycle the second oligodeoxyribonucleotide ligated to the adapter is ligated to site HindIII of the vector. The filling-in of the single-stranded 5'-protruding end and elimination of the 3'-protruding end resulting from the PstI cleavage are carried out simultaneously using Klenow polymerase in the presence of all four deoxyribonucleoside 5'-triphosphates as shown in FIG. 4. After blunt-end ligation, transformation, selection and isolation, a vector is obtained which contains the two oligodeoxyribonucleotides incorporated by means of the adapter so that there is only a single nucleotide (C), originating from site PstI, left at the site of ligation. Thereafter, the whole procedure may be repeated cyclically, as many times as desired; the DNA region obtained can be cut out by BamHI and PstI double digestion after any cycle, and can be treated further as illustrated in FIG. 2, depending on the intended use.

Screening for Recombinants

Screening for the expected recombinants is an unavoidable step in any cloning method, and it is an essential requirement that the desired recombinants should be easily distinguishable from the starting vector and from the other recombinants. For screening and subsequent nucleotide sequencing, we used M13mp phage vectors (Messing J et al. 1981 Nucleic Acids Res. 9, 309; Messing J et al. 1982 Gene 19, 269 and Norrander J et al. 1983 Gene 26, 101), which are widely known and used in the literature. These vectors contain a portion of the lac operon derived from E. coli, i.e. operator, promoter and a DNA region coding for a part of the amino terminal of beta-galactosidase (in the case of mp7 amino acids 1-145 and in the cases of mp8, mp9, mp10, mp11 and their derivatives amino acids 1-59) in a region which is not vital for phage development. This is the so called alpha-fragment of beta-galactosidase, the synthesis of which can be induced by IPTG (isopropyl-beta-D-galactopyranoside). The alpha-fragment itself is enzymatically inactive, but it is able to complement in vivo the omega-fragment of beta-galactosidase to an active enzyme (the omega-fragment is also inactive enzymatically because it lacks amino acids 11-41 of the wild type enzyme). The E. coli host strain lacks the entire chromosomal beta-galactosidase gene ($\Delta$ lac), but it contains an episome part of which codes for the omega-fragment. When this strain is infected with the above-mentioned M13 phage derivatives in the presence of IPTG, the alpha-and omega-fragments complement each other, and a functional beta-galactosidase is obtained. The enzyme activity is detected by means of a lactose analogue X-gal (5-bromo-4-chloro-3-indoyl-beta-galactoside) from which a blue compound is obtained on the action of beta-galactosidase. Accordingly, the M13mp phage derivatives complementing the defective enzyme of the host cell result in a blue plaque.

The complementing ability of the alpha-fragment coded by the M13mp phages is not influenced by the structure of the region adjacent to the amino termini. Therefore, 30-50 bp DNA-regions were inserted into the various M13mp vectors, generally at the site of fourth-sixth amino acid of the alpha-peptide. These DNA regions contain a series of restriction sites (polycloning region) which are not found in the phage DNA. During the design of the polycloning regions, case is generally taken that the reading frame of the alpha-fragment should not be shifted, and that these regions should not contain a termination codon in phase.

If a foreign DNA region is inserted at the polycloning site, two possibilities arise. A blue plaque is formed in high probability if the reading frame of the alpha-fragment is not shifted by the inserted DNA region and the foreign DNA does not contain a termination codon in phase. In the event of a reading frame shift or the presence of a terminator codon in phase, a white plaque is formed. If the length of the (in our case single-stranded) DNA chain is designed in advance, it can be foreseen whether or not the recombinant obtained by cloning will result in a change in colour compared to the cloning vector. If the starting vector and the recombinant result in the same colour, the recombinant may be selected in a random manner. The selection is considerably easier if there is a change in colour, e.g. from blue to white as described above. However, even this colour change does not guarantee a reliable selection of the desired recombinants, for the contaminating non-specific nucleases may be present during the enzymatic steps can cause side-reactions, which result in the same colour change. The white to blue colour change provides an even more reliable selection. In this case a vector is constructed which does contain a polycloning site, but this shifts the reading frame and thus no active alpha-fragment can be synthesized. If a DNA region restoring the reading frame of the alpha-fragment is inserted at the polycloning site, a blue recombinant may be expected. Since it is more probable that the non-specific enzymatic side-reactions result in a white (and not a blue) plaque, this selection is considered the most reliable.

Though the above selection methods are very useful in the screening of recombinants, none of them is entirely satisfactory. Further identification of the recombinants is therefore carried out at molecular level. From a suitably large number of recombinants with the expected colour single-stranded DNA is isolated and subjected to e.g. the C-reaction of the dideoxy sequencing by means of a universal primer for each expected recombinant phage. The phage DNA corresponding to the starting vector is used as a control. If a DNA fragment is inserted, the C-pattern characteristic of the starting vector is shifted upwards on the sequencing gel, and even the length of the inserted DNA fragment may be estimated from the extent of the shift. The recombinant of desired length is then identified by nucleic acid sequencing by the dideoxy method (Sanger F et al. 1977 PNAS USA 74, 5463), all four reactions being used.

The isolation of phage DNA and C-track analysis may be carried out with a large number (50–60 per day) of recombinants simultaneously, while sequencing can be applied to 12–20 recombinants simultaneously. The screening and nucleotide sequence analysis described above can be used not only in the case of M13mp vectors, but also for the screening and analysis of plasmid vectors with analogous properties. For example, pUC plasmids (Vieira J et al. 1982 Gene 19, 259) and their derivatives can be employed in the same manner. In this case, not plaques but antibiotic-resistant (ampicillin-resistant) colonies are obtained and selected on the basis of the colour reaction described above. DNA can be isolated only in a double-stranded form from the recombinants, and the sequence analysis of this by the dideoxy method is somewhat less reliable than in the former case. If desired, however, sequence analysis can be carried out on both DNA strands, by means of universal primers pointing in two opposite directions, so that the final identification based on the nucleotide sequence is fully reliable in this case, too. On the other hand, the pUC plasmids are advantageous in that they are more stable than M13mp vectors, even it they contain a long foreign DNA piece. Due to their double-stranded structure, hybridization with the radioactively labeled form of the oligodeoxyribonucleotide to be cloned can also be used as a first screening step with pUC vectors.

The major advantages of the process described in the invention are as follows:

1. Only one strand of a double-stranded DNA piece need be prepared chemically; the complementary strand is synthesized enzymatically. As concerns the end-product, the only redundant synthetic work involves a short 3'-terminal sequence (usually 5 nucleotides) of the oligodeoxyribonucleotide to be cloned. As this 3'-terminal sequence is characteristic of a given restriction site, it can be prepared in large amount and a small aliquot of this concensus sequence is used as starting material to obtain oligodeoxyribonucleotides with specific sequences.

2. The 5 nucleotide long concensus sequence does not remain in the end-product, as 4 nucleotides are removed during a cloning cycle. Only one nucleotide of the 3'-terminal concensus sequence remains at the site of attachment of the synthetic DNA fragments. This single nucleotide can form an integral part of the final sequence if it is taken into consideration in the planning of the fragmentation of the final DNA molecule and the nucleotide sequence of each fragment. In light of the above, for example, it is sufficient to synthesize a 45 nucleotide long oligodeoxyribonucleotide to obtain a 41 bp double-stranded DNA region (82 nucleotides).

3. It can be planned in advance which of the two strands of the DNA to be prepared can be synthesized chemically more advantageously. Pyrimidine-rich sequences are synthesized more easily than purine-rich ones. The process described in the invention allows choice of the pyrimidine-rich regions as the target of chemical synthesis, with enzymatic synthesis of the purine-rich regions.

4. The order of the enzymatic reactions is such that the semi-synthetic DNA pieces are attached to one another in the appropriate orientation inside the cloning vector. After the fragments have been linked, there are no sequence remains characteristic of the restriction site used for cloning.

5. Once a single-stranded oligodeoxyribonucleotide is inserted into a vector and cloned, the different possibilities of the cyclic performance allow extension of the length of the cloned DNA piece with further incoming oligodeoxyribonucleotides up to a kilobase order of magnitude. The number of cycles depend on the strategy employed. If the starting vector contains a number of closely located unique restriction sites resulting in 3'-protruding ends (route B1, FIG. 4), the number of cycles is determined by the number of such sites. When an adapter is used (route B2, FIG. 5), the number of cycles is in principle unlimited.

6. There is no need to purify the single-stranded oligodeoxyribonucleotides to homogeneity. In fact, cloning is a final, entirely reliable purification method, since the recombinant obtained by ligation of a single molecule to a vector and cloning results in an entirely homogeneous fragment. In this way, the members of a heterogeneous oligodeoxyribonucleotide population which can not otherwise be separated from each other by physical-chemical methods, may be isolated in pure form.

7. Screening for recombinants and their analysis is relatively simple. An appropriate selection of the vector-host system on the basis of phenotypic properties (e.g. colour of plaque or colony) is suitable for the high-probability identification of the expected recombinants. Additionally, nucleic acid sequencing (the dideoxy method) allows a final, highly reliable identification of the recombinants obtained.

EXAMPLES

The invention will be further illustrated by the following, non-limiting examples, relating to the ligation of five single-stranded synthetic oligodeoxyribonucleotides:

| | |
|---|---|
| GATCCGGTACCGAGCTCCTGCA | a 22-mer, |
| C(T)(T)TTGGTACCGAGCTCCTGCA | the 21-mer member of 20 + 21 + 22-mer mixture, |
| CATGTTTGTTAACCAGCACCTGTGCGGCTCTCACCTGCA | a 39-mer, |
| CATGGGCATCGTTGAACAGTGTTGTACTTCTATCTGCTCTCTGCA | a 45-mer, |
| TTTACCAGCTTGAGAACTACTGTAACTAGCCTGCA | a 35-mer | to various M13mp vectors, the enzymatic synthesis of the respective complementary strands and cloning of the double-stranded DNA fragments. The first four oligodeoxyribonucleotides were ligated to the site PstI of the appropriately cleaved vector directly, while the fifth oligodeoxyribonucleotide was ligated and cloned by means of an adapter (route B2):

Chemical synthesis of the single-stranded oligodeoxyribonucleotides was performed by means of the most efficient variants of the phosphate-triester solid phase method (Efimov VA et al. 1982 Nucleic Acids Res. 10, 6675 and Sproat BS et al. 1983 Tetrahedron Letters 24, 5771), starting from monomer and/or dimer building blocks.

M13mp8 (Messing J et al. 1982 Gene 19, 269), M13mp10 (Norrander J et al. 1983 Gene 26, 101) and M13mpW324 (constructed in our laboratory from M13mp8 by inserting a shorter DNA piece than the original one between the sites BamHI and PstI, the product giving a white plaque) were employed as starting vectors. The recipient E. coli strain was JM101 (F' traD36 lacI⁹ lacZΔM15 proAB+/Δ (lac-ProAB) supE thi) (Messing J et al. 1981 Nucleic Acids Res. 9, 309). Of the starting vectors with known chemical structures, M13mp8 replicative form DNA (Cat. No. 27-1528-01) and M13mp10 replicative form DNA (Cat. No. 27-1537-01) were purchased from Pharmacia P-L. Biochemicals.

Figure 7:
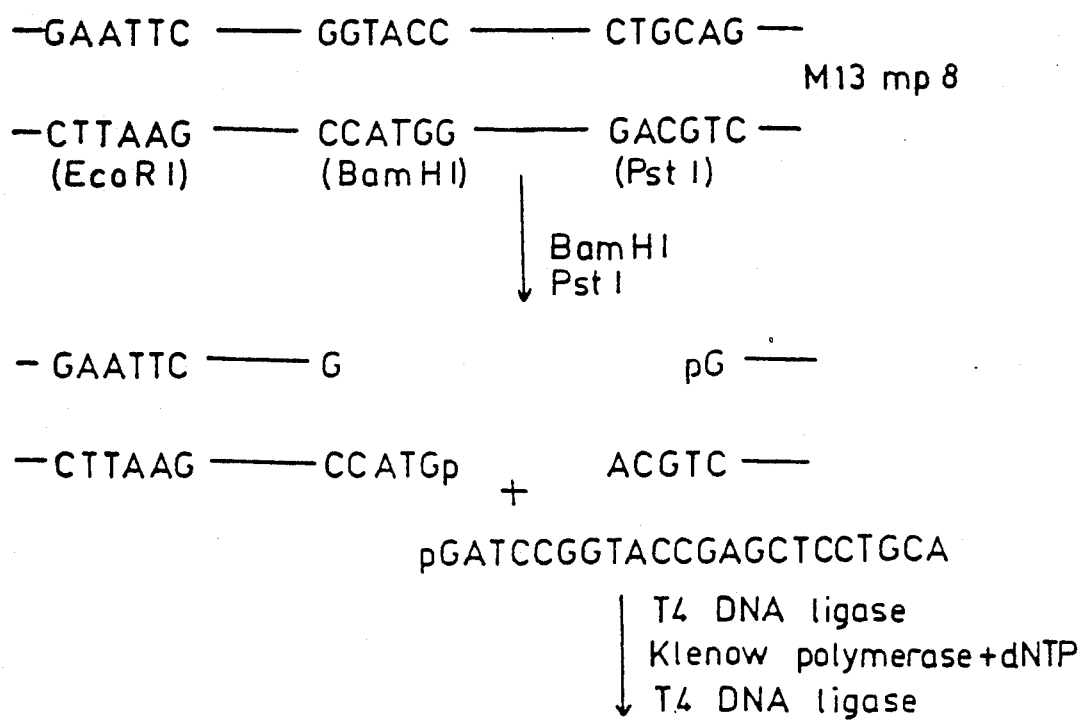
FIG. 7 shows cleaving of the M13mp8 replicative form with BamHi and PstI and ligating the resulting large fragment with the 5'-phosphorylated 22-mer.
Figure 9:
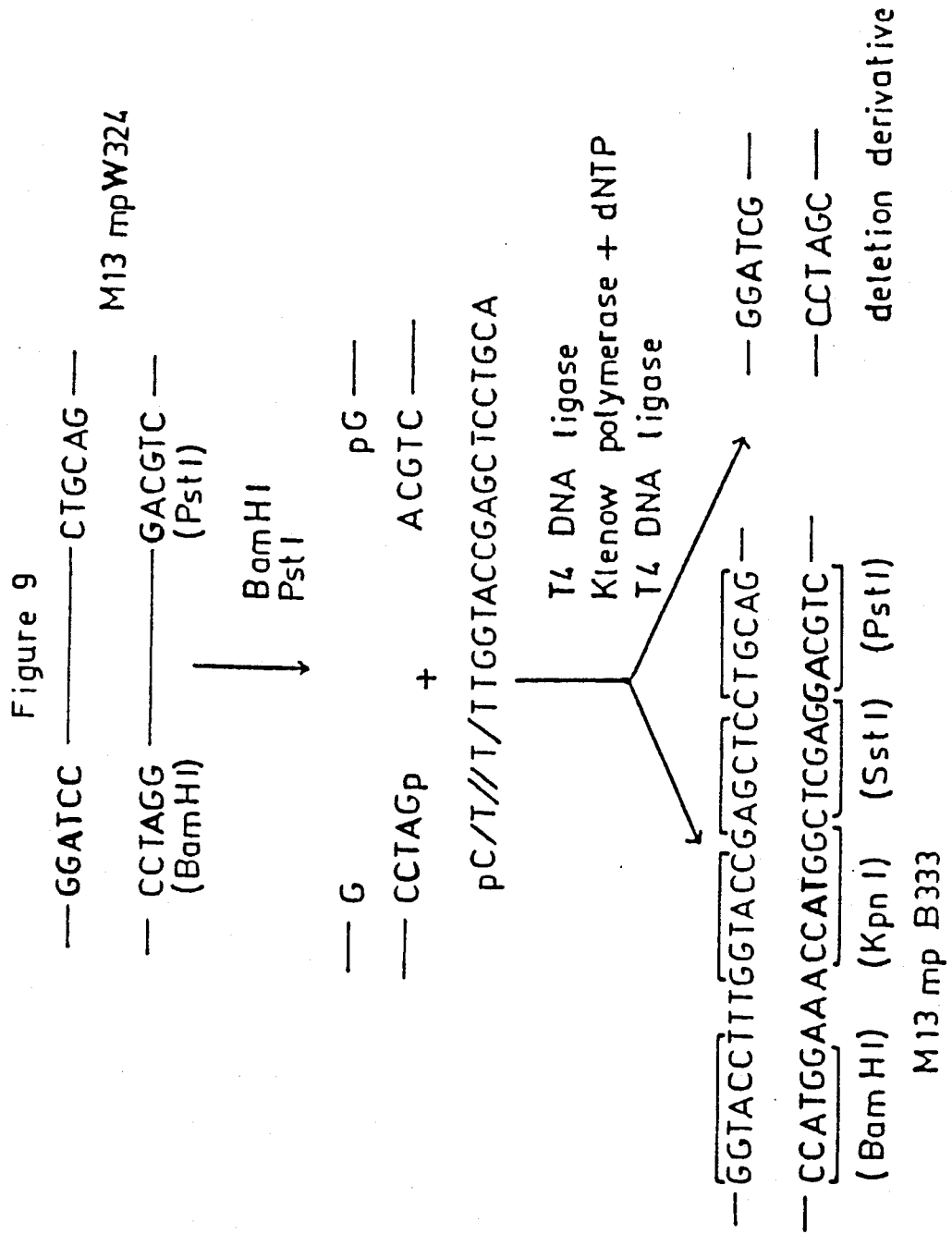
FIG. 9 shows the preparation of a recombinant code for an alpha-peptide derivative capable of alpha-complementation.
Figure 10:
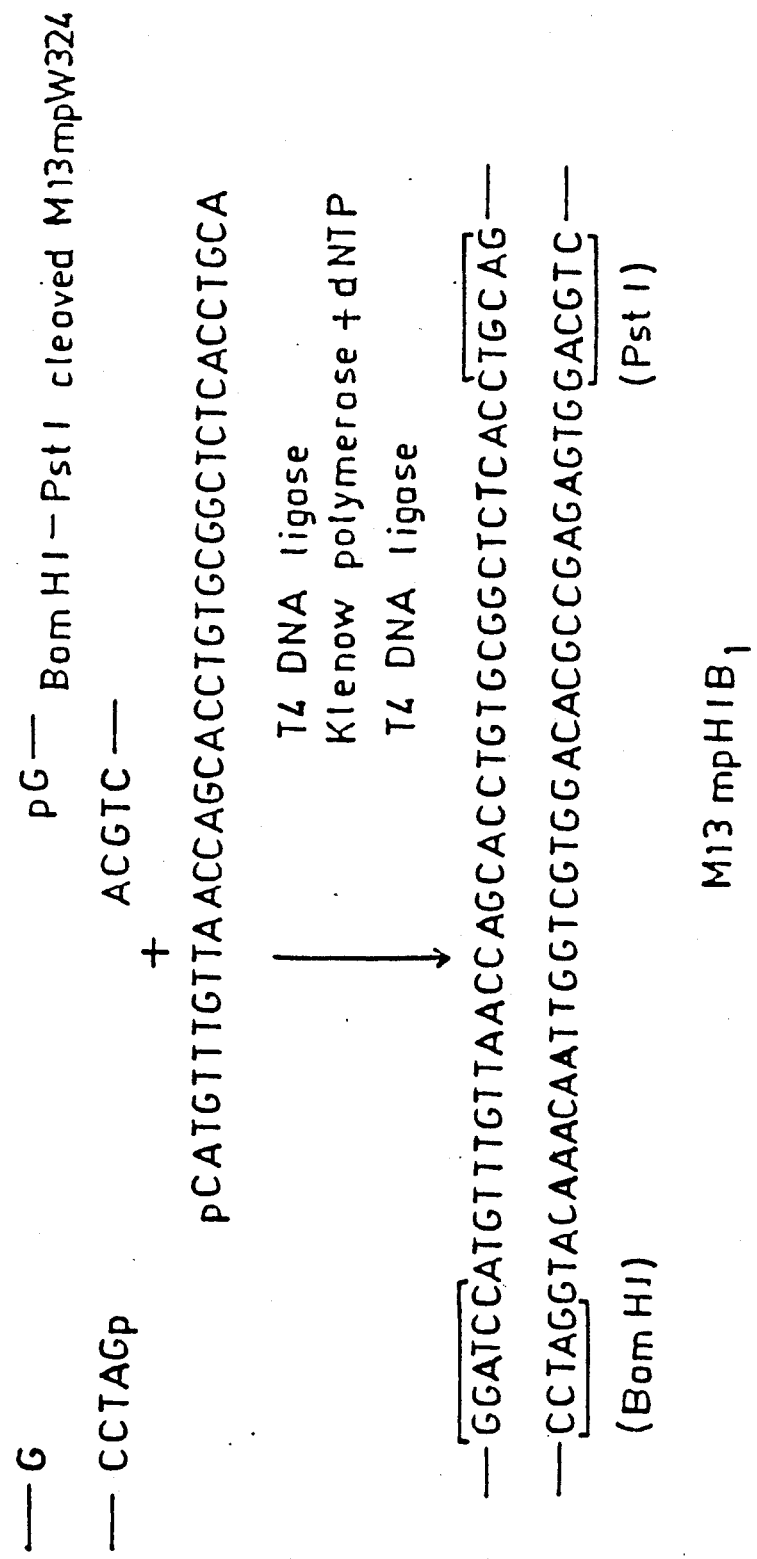
FIG. 10 shows the preparation of a recombinant, designated M13mpHIB, which contains a segment of an artificial gene coding for the B chain of human insulin.
Figure 11:
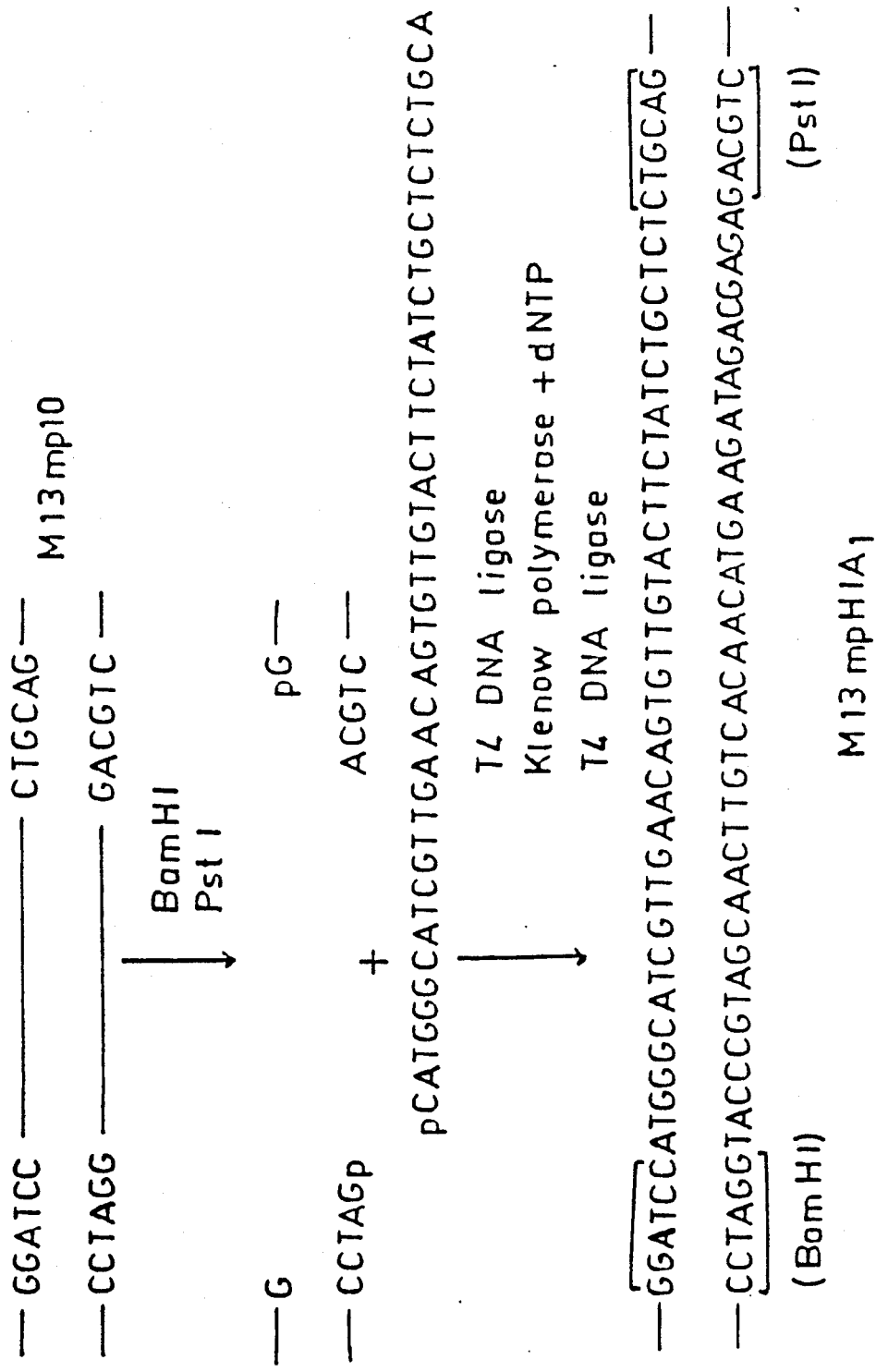
FIG. 11 shows the preparation of M13mpHIA, which contains a part of an artificial gene coding for the A chain of human insulin.
Figure 12:
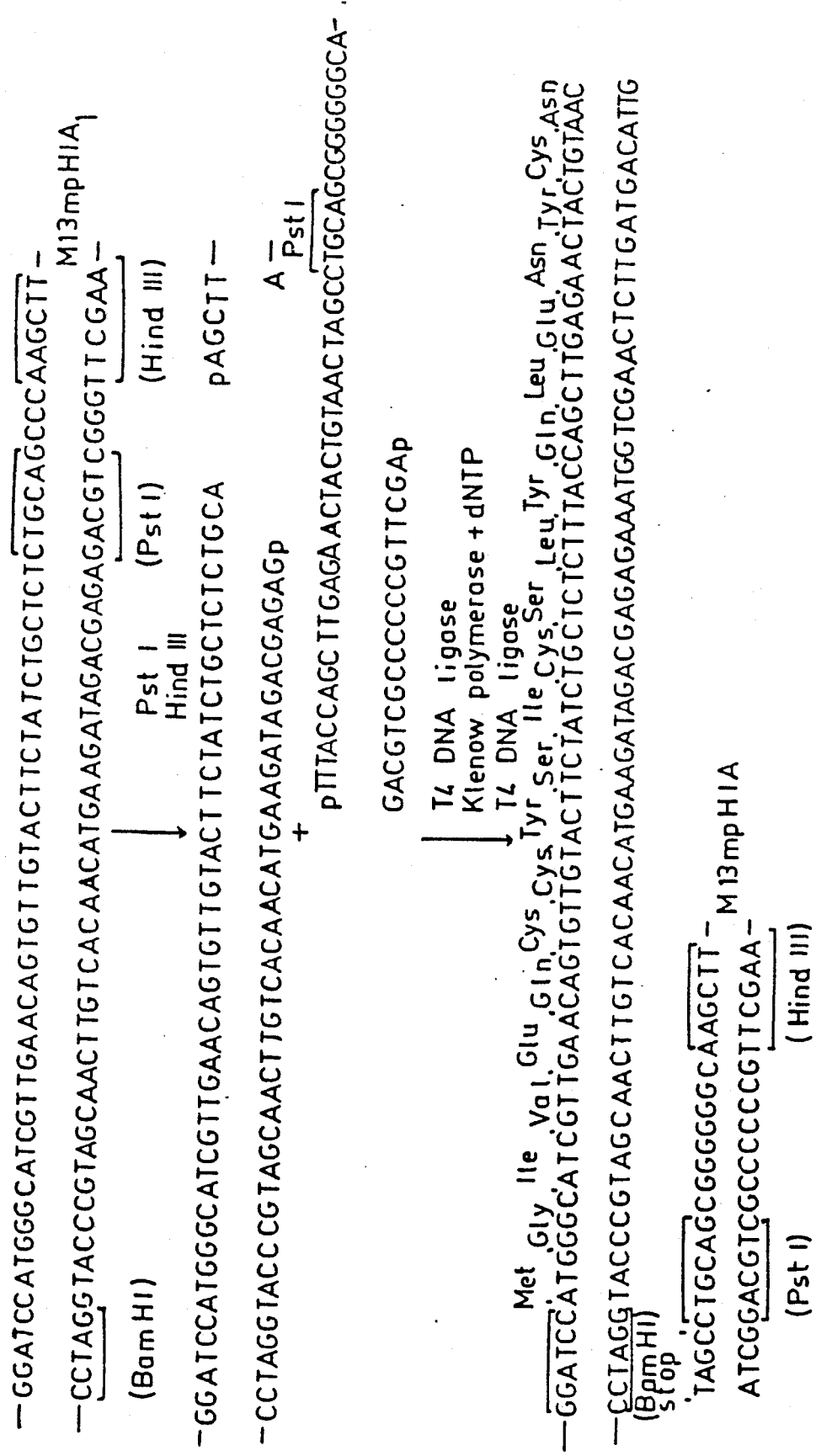
FIG. 12 shows the preparation of the M13mpHIA clone which contains a DNA segment capable of human insulin.

The preparations of various M13mp derivatives are illustrated as follows:

| | | |
|---|---|---|
| M13mpW801 | Example 1 | FIG. 7 |
| M13mpW324 | Example 2 | FIG. 8 |
| M13mpB333 | Example 2 | FIG. 9 |
| M13mpHIB₁ | Example 3 | FIG. 10 |
| M13mpHIA₁ | Example 4 | FIG. 11 |
| M13mpHIA | Example 5 | FIG. 12 |

Instead of the M13mp vectors, other polylinker vectors having similar selection properties, e.g. pUC derivatives or pEMBL derivatives (Dente L et al. 1983 Nucleic Acids Res. 11, 1645), may be employed as well.

Sources of the enzymes used in the examples: The restriction endonucleases were manufactured by New England Biolabs (NEB), the T4 DNA ligase by Cambridge Biotechnical Laboratory (CBL), the DNA polymerase large fragment (Klenow polymerase) either by CBL or Boehringer Mannheim. The enzymatic reactions, if not otherwise stated, were carried out in accordance with the guidelines given by the manufacturers.

Replicative forms were isolated from the M13mp derivatives (Birnboim HC et al. 1979 Nucleic Acids Res. 7, 1513). After cleavage with two different restriction enzymes, the large fragment obtained from the vector was purified either by agarose gel electrophoresis and subsequent elution (Maniatis T et al. 1982 Molecular Cloning, Cold Spring Harbor Laboratory N.Y., pp. 164-170) or by precipitation with ammonium acetate. Precipitation with ammonium acetate was performed as follows. After restriction digestion, the reaction mixture containing about 1 μg of DNA was subjected to heat treatment at 65° C. for 10 min, made up to 100 μl with water and extracted with 100 μl of phenol at room temperature. To the aqueous phase 10 μl of 3M sodium acetate solution (pH 5.2) and 250 μl of ethyl alcohol were added, and after quick freezing (liquid air, 5 min) the mixture was centrifuged (12,000 r.p.m., 5 min). The precipitate was dissolved in 100 μl of water and 50 μl of 7.5M ammonium acetate, after which 200 μl ethyl alcohol was added to the solution, which was then cooled to −70° C. for 15 min and centrifuged as described above. The steps of dissolution and precipitation were then repeated. The precipitate was next washed with 1 ml of cold ethyl alcohol, dried and dissolved in sterile water.

General Procedure for Cloning the Oligodeoxyribonucleotides

After cleavage with two appropriate restriction enzymes, the purified vector (20-50 ng) was ligated with a 5'-phosphorylated single-stranded oligodeoxyribonucleotide, or with the adduct obtained by ligation of the 5'-phosphorylated single-stranded oligodeoxyribonucleotide and the PstI/HindIII adapter, in 10 μl of reaction mixture (50 mM Tris-HCl, pH 7.5, 10 mM MgCl₂, 10 mM dithiotreitol, 1 mM ATP), in the presence of 0.2 units of T4 DNA ligase at 15° C. for 12 to 20 hr. The reaction mixture was kept at 65° C. for 5 min and briefly centrifuged (10-30 s, 12,000 r.p.m.), and 1 μl of a deoxyribonucleoside 5'-triphosphate mixture containing dATP, dCTP, dGTP and TTP each at 1 mM concentration (1 mM dNTP mixture) and 1 μl of 0.5 unit/μl Klenow polymerase was added. The mixture was allowed to stand at room temperature for 10 min and then heated to 65° C. for 5 min. After a brief centrifugation, 4.5 μl of sterile water, 1 μl of 10 mM ATP, 1 μl of 100 mM dithiotreitol and 1 μl of a buffer (500 mM Tris-HCl, pH 7.5, 100 mM MgCl₂) were added. The mixture was cooled to 15° C. and 0.5 μl of T4 DNA ligase (2 units/μl) was added. After incubation at 15° C. for 12-24 hr, JM 101 E. coli cells were transformed with the reaction mixture (Dagert M et al. 1979 Gene 6, 23 or Hanahan DJ 1983 J. Mol. Biol. 166, 557). The transformed cell suspension was poured onto TY plates at 45° C. in the presence of X-gal and IPTG, using 3 ml of top agar (Winter G et al. 1980 Nucleic Acids Res. 8, 1965) and the plates were incubated at 37° C. for 8–16 hr. Single-stranded DNA was prepared from the plaques with the desired colour (8–60 plaques) and T- or C-track analysis was carried out for each phage DNA (Sanger F et al. 1981 J. Mol. Biol. 143, 161). In this way the recombinants containing the desired DNA fragment were selected and the nucleotide sequences of these recombinants were determined by the dideoxy method (Sanger F et al. 1977 PNAS USA 74, 5463). From one of the clones containing the desired sequence, double-stranded replicative form was prepared for the further steps.

Ligation of the 35-mer TTTACCACCTT-GAGAACTACTGTAACTAGGCTGCA to the PstI/HindIII adapter:

15 pmoles of 5'-$^{32}$P-phosphate AGCTTGCCCCCCGCTGCAG and 15 pmoles of 5'-$^{32}$P-phosphate GCGGGGGGCA were dissolved in 10 μl of water and kept at 60° C. for 30 min. Next, 50 pmoles of the 5'-$^{32}$P-phosphate 35-mer (in 5 μl of aqueous solution) was added, and the solution was kept at 37° C. for 30 min and then lyophilized (FIG. 6).

The lyophilization residue was dissolved in 20 μl of buffer (50 mM Tris-HCl, pH 7.5, 10 mM MgCl$_2$, 10 mM dithiotreitol, 1 mM ATP), 0.25 μl of T4 DNA ligase (2 units/μl) was added, and ligation was carried out at 15° C. for 24 hr. After precipitation with 50 μl of ethyl alcohol and drying, the precipitate was dissolved in 20 μl of HindIII buffer and left to stand at 37° C. for 2 hr with 20 units of HindIII enzyme. The 35-mer ligated to the PstI/HindIII adapter was obtained from the reaction mixture through electrophoresis on 10% non-denaturing polyacrylamide gel (400 V, 6–8 hr at room temperature) and subsequent elution from the band selected by means of radioautography (Edge MD et al. 1981 Nature 292, 756).

EXAMPLE 1

Cloning of the 22-mer
GATCCGGTACCGAGCTCCTGCA

The M13mp8 replicative form was cleaved with BamHI and PstI enzymes and, after separation on 0.5% agarose gel and electroelution, the resulting large fragment (about 25 ng) was ligated with the 5'-phosphorylated 22-mer (2.5 pmoles). The steps were carried out as in the general cloning procedure, and selection was performed for white plaques in a blue background. In a random manner, 13 of the resulting white plaques were selected and used to prepare single-stranded phage DNA. T-track analysis revealed that 9 of the 13 selected recombinants displayed the shift characteristic of the incorporated 22-mer. These 9 were subjected to nucleic acid sequencing, and 7 of them were found to contain the sequence of the 22-mer between sites BamHI and PstI. The preparation of one of such vector (M13mpW801) is illustrated in FIG. 7. It is characteristic of M13mpW801 that as a phage it gives a white plaque on a JM101 lawn in the presence of X-gal and IPTG, while its replicative form contains the recognition sequence of three adjacent restriction enzymes (KpnI, SstI and PstI) resulting in 3'-protruding ends. It can therefore be applied as the starting vector of cyclic cloning via route B1, through utilization of EcoRI and the above three restriction sites, similarly as in FIG. 4.

EXAMPLE 2

Cloning of the 20, 21 and 22-mer oligodeoxyribonucleotides, and selection for recombinants containing the 21-mer This example demonstrates how it is possible to apply the cloning method to select a desired component (in the given case the 21-mer) from a heterogeneous oligodeoxyribonucleotide mixture (here a mixture of the 20, 21 and 22-mers). The mixture may be characterized by the formula C(T)(T)TTGGTACCGAGCTCCTGCA, in which the oligodeoxyribonucleotides CTTGGTACCGAGCTCCTGCA, CTTTGGTACC-GAGCTCCTGCA and CTTTTGGTACC-GAGCTCCTGCA are present in approximately equimolar proportions.

An M13mp8 derivative, M13mpW324, was used as starting vector; in this sites BamHI and PstI are situated at different distances from those in M13mp8. The phage originating from M13mpW324 resulted in a white plaque on the JM101 E. coli lawn (FIG. 8).

The M13mpW324 replicative form was cleaved with BamHI and PstI enzymes and the large fragment was isolated by precipitation with ammonium acetate. As described in the general procedure, about 50 ng of the large fragment was mixed with the 5'-phosphorylated form of an oligodeoxyribonucleotide mixture of the 20, 21 and 22-mers (10 pmoles), and the previously described cloning steps were carried out. After transformation, selection was performed for blue plaques, these being expected only in the case of incorporation of the 21-mer component. 8 of 35 blue plaques were selected in a random manner, and the single-stranded phage DNA was isolated from these and subjected to C-track analysis. Of these 8 recombinants, 2 gave C-tracks to be expected in the case of 21-mer incorporation. Sequencing demonstrated that both recombinants contained the sequence corresponding to the 21-mer between sites BamHI and PstI. One such recombinant was designated M13mpB333. The other 6 blue plaques originated from a deletion recombinant formed through filling-in of site BamHI with polymerase, cleavage of the non-ligated 3'-protruding end of site PstI as a consequence of the 3'5' exonuclease activity of Klenow polymerase, and further ligation; this recombinant code for an alpha-peptide derivative capable of alpha-complementation (FIG. 9).

It is characteristic of the M13mpB333 derivative obtained that in phage form it gives a blue plaque on a JM101 lawn (in the presence of X-gal and IPTG), while its replicative form contains the recognition sequence of three adjacent restriction enzymes (KpnI, SstI and PstI) resulting in 3'-protruding ends. Similarly to the M13mpW801 vector described in example 1, therefore, the replicative form permits cyclic cloning through the use of sites BamHI, KpnI, SstI and PstI, via route B1, but with a different colour selection.

EXAMPLE 3

Cloning of the 39-mer
CATGTTTGTTAACCAG-CACCTGTGCGGCTCTCACCTGCA

The M13mpW324 replicative form was cleaved with BamHI and PstI enzymes, and the large fragment was purified by precipitation with ammonium acetate. About 40 ng of the large fragment was reacted with 50 pmoles of the 5'-phosphorylated 39-mer through the steps described in the general procedure. After transformation into the JM101 *E. coli* strain, selection was performed for blue plaques in a white background. Single-stranded phage DNA was isolated from 20 blue plaques. C-track analysis showed that 19 recombinants exhibited 39-mer incorporation. The sequencing of 7 such recombinants revealed that 5 contained the sequence corresponding to the 39-mer. One such recombinant, which contains a segment of an artificial gene coding for the B chain of human insulin, was designated M13mpHIB$_1$ (FIG. 10).

EXAMPLE 4

Cloning of the 45-mer
CATGGGCATCGTTGAACAGTGTTGTACTT-
CTATCTGCTCTCTGCA

The M13mp10 replicative form was cleaved with BamHI and PstI enzymes, and the large fragment was purified by precipitation with ammonium acetate. About 25 ng of the cleaved vector was reacted with 10 pmoles of the 5'-phosphorylated 45-mer as in the general procedure (FIG. 11). The reaction mixture was transformed into the JM101 *E. coli* strain, and blue plaques were selected in a random manner as the starting vector also gives rise to blue plaques. Single-stranded phage DNA was isolated from 51 blue plaques. On C-track analysis, 24 of the examined 51 clones displayed the shift characteristic of the incorporated 45-mer, 20 proved to be starting M13mp10, and 7 were deletion derivatives obtained in a similar way as in example 2. Sequencing was performed on 14 of the 24 recombinants, and 8 of these 14 clones contained the sequence corresponding to the 45-mer. One such clone, which contains a part of an artificial gene coding for the A chain of human insulin, was designated M13mpHIA$_1$.

EXAMPLE 5

Cloning of the 35-mer
TTTACCAGCTTGAGAACTACTGTAAC-
TAGCCTGCA

This example illustrates cloning via route B2, with application of the synthetic adapter. The M13mpHIA$_1$ vector obtained in example 4 was used as starting vector. The above cloned 45-mer and the synthetic 35-mer were joined to each other with help of the linearized M13mpHIA$_1$ vector and the synthetic adapter. The resulting vector contains a complete artificial gene coding for the A chain of human insulin.

The M13mpHIA$_1$ vector was cleaved with PstI and HindIII enzymes, and the large fragment was purified by precipitation with ammonium acetate. The 35-mer ligated to the PstI/HindIII adapter was mixed with about 10 ng of the cleaved vector, and the further reactions were carried out as in the general procedure. White plaques are expected after transformation of the reaction mixture into the JM101 *E. coli* strain. A total of 4 white plaques were obtained. 12 of these were selected, and single-stranded phage DNA was prepared from them. Sequencing revealed that 5 of these recombinants contained the desired 35-mer, linked to the 41 nucleotide long region of the 45-mer cloned in example 4. The M13mpHIA clone (FIG. 12) obtained contains a DNA segment capable of coding for the A chain of human insulin. The amino acid sequence taken from the nucleotide sequence in the Figure merely denotes the coding ability of the cloned DNA region, but not that the expression of M13mpHIA results in a functional human insulin A chain. However, expression of the human insulin A chain is permitted by cutting-out of the coding region from the M13mpHIA vector, and by its insertion into an expression vector in an appropriate reading frame.

We claim:

1. A process for the preparation of oligo- and polydeoxyribonucleotides comprising inserting a single-stranded DNA piece into a cloning vector, said vector containing a number of closely located recognition sequences of restriction enzymes giving a 3'-protruding end, each present only once in the said vector and which, following cleavage with two corresponding restriction enzymes, produces a linearized vector containing a 5'-protruding end and a 3'-protruding end, said single-stranded DNA piece being inserted into the linearized vector such that, after ligation, the linear vector containing said single-stranded DNA contains 5'-protruding regions at both ends, and synthesizing the complementary strand of said single-stranded DNA piece entirely enzymatically in the presence of deoxyribonucleoside 5'-triphosphates in said cloning vector.

2. The process of claim 1, in which the single-stranded DNA piece is ligated to the vector by means of an adapter having a double-stranded region, a 5'-protruding end complementary to a unique cleavage site of the vector which results in a 5'-protruding end, and a 3'-protruding end characteristic of a restriction enzyme the recognition sequence of which is not present in the linearized vector, and from which sequence at most one or two nucleotides remain in the resulting DNA region at the site of attachment of the cloned DNA fragments following enzymatic synthesis and cloning.

3. The process of claim 1, in which the vector is selected from the group consisting of M13mpW801 and M13mpW324.

4. An adapter having a double-stranded region, a 5'-protruding end complementary to a unique cleavage site of the vector which results in a 5'-protruding end, and a 3'-protruding end characteristic of a restriction enzyme the recognition sequence of which is not present in the linearized vector, and from which sequence at most one or two nucleotides remain in the resulting DNA region at the site of attachment of the cloned DNA fragments following enzymatic synthesis and cloning.

5. The process of claim 1, in which the single-stranded DNA piece is ligated to an appropriately cleaved cloning vector, the complementary strand of said single-strand DNA is synthesized in the presence of deoxyribonucleoside 5'-triphosphates, the vector is recircularized to form a modified vector, bacterial cells are transformed with the modified vector, transformant clones of bacteria are selected and the modified vector is isolated from the transformant clones.

6. The process of claim 5 wherein the desired oligo- or polydeoxyribonucleotide is cut out of the isolated modified vector in a double-stranded form and a double-stranded DNA having a linking end suitable for further use is isolated.

7. The process of claim 5 wherein the desired oligo- or polydeoxyribonucleotide is cut out of the isolated modified vector in a double-stranded form, the double-stranded oligo- or polydeoxyribonucleotide with suitable linking end and a single-stranded oligo- or polynucleotide piece are simultaneously ligated into a vector, the complementary strand of said single-stranded oligoor polynucleotide piece is synthesized, and the vector is recircularized and cloned.

8. The process of claim 5 wherein the isolated modified vector is linearized by cleavage at the insertion site of the ligated DNA piece, a single-stranded oligo- or polynucleotide piece is ligated to the vector at a different, closely located site, the complementary strand of said single-stranded oligo- or polynucleotide piece is synthesized, and the vector is recircularized and cloned.

9. The process of claim 5, in which an M13mp derivative is used as the vector and the bacterial strain *E.coli* JM101 is transformed.

10. The process of claim 5, in which the clones containing the desired oligo- or polydeoxyribonucleotide are selected on the basis of either destruction or restoration of the alpha-peptide function of beta-galactosidase.

* * * * *